US00PP09579P

United States Patent [19]

Endisch et al.

[11] Patent Number: Plant 9,579

[45] Date of Patent: Jun. 11, 1996

[54] GERANIUM PLANT NAMED 'MIRO'

[75] Inventors: Gerd Endisch, Geranienweg, D-76767 Hagenbach; Ursula Endisch-Burmeister, Bad Kreuznach, both of Germany; Wolf Endisch, Valle Guerra, Spain

[73] Assignee: Gerd Endisch, Hagenbach, Germany

[21] Appl. No.: 384,142

[22] Filed: Feb. 6, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,610 7/1991 Trees ..... Plt./87.12

P.P. 7,936 8/1992 Hanes ..... Plt./87.12

*Primary Examiner*—James R. Feyrer

*Attorney, Agent, or Firm*—Willian Brinks Hofer Gilson & Lione

[57] ABSTRACT

A new and distinct cultivar of geranium known by the cultivar name 'Miro' is characterized by a salmon flower color, a semi-double flower form, dark foliage, medium zonation and a compact habit.

1 Drawing Sheet

BACKGROUND OF THE NEW PLANT

The present invention comprises a new and distinct cultivar of geranium botanically known as *Pelargonium zonale,* and hereinafter referred to by the cultivar name 'Miro'.

'Miro' is a product of planned breeding program which had the objective of creating new geranium cultivars with salmon flower color, semi-double flower form, dark foliage, early flower response.

'Miro' was originiated from a hybridization made in a controlled breeding program in Hagenbach, Germany, in 1991. The female parent was 'Hagenbacher Lachs', characterized by its salmon-pink flower color, semi-double flower form and medium green foliage. The male parent of 'Miro' was 'Hoennefrühling', characterized by its light salmon-pink flower color, single flower form, strong zonation and very early flower response. Neither of the parent plants is patented or presently available on a commercial basis. Its semi-double flower distinguishes 'Miro' from 'Hoennefr ühling' and its dark foliage distinguishes 'Miro' from the medium green foliage of 'Hagenbacher Lachs'.

'Miro' was discovered and selected as one flowering plant within the progeny of the stated cross by the inventors in September 1992 in a controlled environment in Hagenbach, Germany.

BACKGROUND OF THE NEW PLANT

The first act of asexual reproduction of miro was accomplished when vegetative cuttings were taken from the initial selection in January 1993 in a controlled environment in Hagenbach, Germany, by a technician working under formulations established and supervised by Gerd Endisch.

Horticultural examination of selected units initiated in May 1983 had demonstrated that the combination of characteristics as herein disclosed for 'Miro' are firmly fixed and are retained through successive generations of asexual reproduction.

'Miro' has not been observed under all possible environmental conditions. The phenotype may vary significantly with variations in environment such as temperature, light intensity, and day length. The following observations, measurements, and comparisons describe plants grown in Hagenbach, Germany, under field conditions which approximate those generally used in commercial practice. The dimensions and measurements given below are approximate.

The following traits have been repeatedly observed and are determined to be basic characteristics of 'Miro' to distinguish this geranium as a new and distinct cultivar:

1. salmon flower color
2. semi-double flower form
3. dark Foliage
4. medium zonation
5. compact habit Of the many commercial cultivars known to the present inventor, the most similar in comparison to 'Miro' is 'Unica.'. Reference is made to Chart A below which compares certain characteristics of 'Micro' to those same characteristics of 'Unica'. In comparison to 'Unica', 'Miro' exhibits leaf zonation, earlier flowers response and better salmon color.

BRIEF DESCRIPTION OF THE DRAWINGS

The accompanying photographic drawing shows typical flower and foliage characteristics of 'Miro' with colors being as true as possible with illustrations of this type.

DETAILED BOTANICAL DESCRIPTION

In the following description color references are made to The 'Royal Horticultural Society Color Chart(RHS). The color values were determined indoors from plants grown outdoors in August 1994 in Hagenbach, Germany, or Hannover (Bundessortenamt).

Classification:

*Botanical.*—A hybrid of the species *Pelargonium zonale.*

*Commercial.*—Zonal geranium, cv. 'Miro'.

Inflorescence:

*Umbel.*—Comprises approx. 58 flowers.

*Average diameter.*—Approx. 92 mm.

*Average depth.*—Approx. 45 mm.

*Peduncle length.*—Approx. 160mm.

*Spring flowering response period.*—In Hannover (Bundessortenamt) in 1994, first flower 20 April; flower opened 13 weeks after planting of unrooted cuttings.

*Outdoor flower production.*—The flower count in 1993 indicated between 50–55 flowers per plant for May 15 through August 15 observation period.

*Durability.*—: Medium rain resistance.

Corolla:

*Blooming habit.*—Continuous; until frost destroys plant.

*Average diameter.*—Aprox. 38–40 mm.

*Form.*—Semi-double; cup shaped when bloom first opens, fattening to shallow cup at maturity.

*Petals.*—Normally nine.

*Color (General tonality from a distance of three meters).*—Salmon, color will not fade with age.

*Color of top surface of upper and lower petals.*—RHS 43 C (middle and base); RHS 52 D (near margin).

*Color of bottom side of upper petals.*—RHS 43 D.

*Color of bottom side of lower petals.*—RHS 48A.

*Pedicel length.*—Approx. 26–28 mm.

*Pedicel color.*—Red (anthocyanin colored).

*Petaloids.*—0–3, colored as the petals.

*Persistence.*—Non-shattering flower.

Bud:

*Size.*—Approx. 1.5–2.0 cm across.

*Shape.*—Initially ovate.

*Color.*—Green with anthocyanin at the base.

*Sepals.*—Five, pointed linear lanceolate; approx. 8 mm in length.

Reproductive organs:

*Stamens.*—Anthers: 6–8 in number.

*Filaments: Approx.* 6–8 mm in length; white.

*Pollen: Orange-red.*

*Pistil.*—No.: One. Length: Approx. 8 mm. Stigma: 5 lobes; red. Style: 3 mm in length, purplish-red, pale green at the base. Ovaries: Pale green. Fruit: Partially fertile.

Plant:

*Foliage.*—Abundant quantity with medium zonation. Size: Approx. 10–11 cm across (fully extended). Shape: Leaves are reniform in plan, slightly upwardly cupped due to close spacing and high density due to short internodes length. Ribs and veins: Distinct venation on lower side, no prominent difference on upper surface. Margin: Bicrenate. Texture: Leathery and pubescent. Color (upper surface): Dark green RHS 137 A/B. Color (zonation): RHS 200 C (Brown). Color (bottom surface): RHS 138 A. Petioles: Approx. 8 cm in length; green.

*General appearance and form.13* Bushy; medium-compact. Internode length: Approx. 22 mm. Branching pattern: Very good self-branching characteristic; 15 branches observed, 15 August 94 Height: Approx. 16–18 cm from media surface.

CHART A

| | New Cultivar Name: 'Miro' | Comparison Cultivar Name: 'Unica' |
|---|---|---|
| Zonation | medium | none |
| Flower response | 20 April 94 | 28 April 94 first flower |
| Flower color | better salmon color stable | fades with age |

What is claimed is:

1. A new and distinct cultivar of geranium plant known as 'Miro', as described and illustrated and particularly characterized by a salmon flower color, a semi-double flower form, dark foliage, medium zonation and a compact habit.

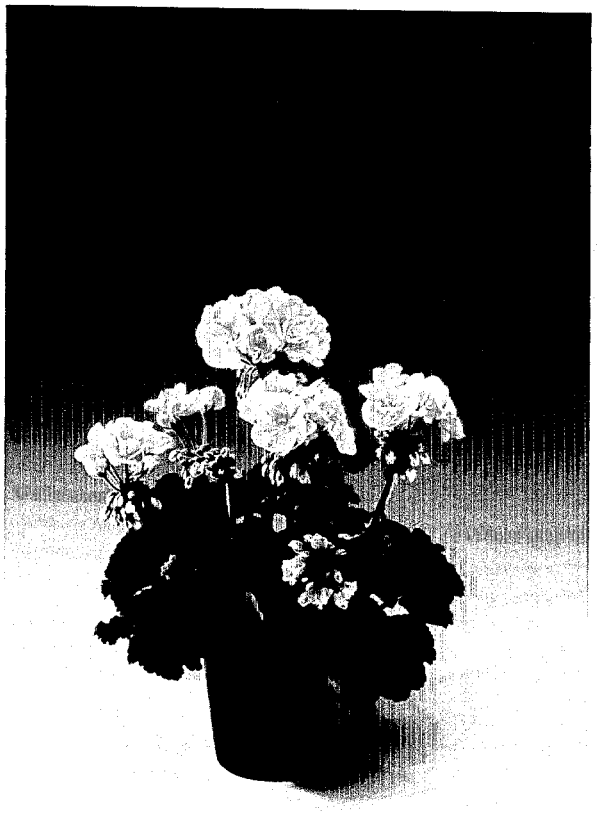

* * * * *